United States Patent
Torii et al.

(10) Patent No.: US 11,547,953 B2
(45) Date of Patent: Jan. 10, 2023

(54) METHOD OF PRODUCING EXTRACT AND EXTRACTION RESIDUE OF BIOLOGICAL MATERIAL, EXTRACT, AND EXTRACTION RESIDUE

(71) Applicant: RICOH COMPANY, LTD., Tokyo (JP)

(72) Inventors: Shogo Torii, Shizuoka (JP); Satoshi Shinohara, Shizuoka (JP); Shogo Suzuki, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 72 days.

(21) Appl. No.: 16/980,728

(22) PCT Filed: Mar. 12, 2019

(86) PCT No.: PCT/JP2019/010077
§ 371 (c)(1),
(2) Date: Sep. 14, 2020

(87) PCT Pub. No.: WO2019/176958
PCT Pub. Date: Sep. 19, 2019

(65) Prior Publication Data
US 2021/0001247 A1    Jan. 7, 2021

(30) Foreign Application Priority Data

Mar. 16, 2018  (JP) .............................. JP2018-050228
Mar. 16, 2018  (JP) .............................. JP2018-050256
(Continued)

(51) Int. Cl.
*B01D 11/02* (2006.01)
*B01D 37/00* (2006.01)

(52) U.S. Cl.
CPC ...... *B01D 11/0288* (2013.01); *B01D 11/0296* (2013.01); *B01D 37/00* (2013.01)

(58) Field of Classification Search
CPC ............ B01D 11/0288; B01D 11/0296; B01D 11/028; B01D 11/0219; B01D 11/0257;
(Continued)

(56) References Cited

U.S. PATENT DOCUMENTS 2,560,935 A  *  7/1951  Dickinson ............... C11B 1/104
554/20
5,830,738 A     11/1998  Thomas et al.
(Continued)

FOREIGN PATENT DOCUMENTS

CN        101484562         7/2009
JP        2000-128792       5/2000
(Continued)

OTHER PUBLICATIONS

Renil Anthony, Solvent extraction and characterization of neutral lipids in *oocystis* sp., Published in Energy Research, Jan. 20, 2015. (Year: 2015).*
(Continued)

*Primary Examiner* — Joseph W Drodge
(74) *Attorney, Agent, or Firm* — Grüneberg and Myers, PLLC (57) ABSTRACT

A method of producing an extract of an animal-derived or plant-derived biological material includes: extracting a component in the biological material using liquefied dimethyl ether for the biological material to obtain a liquefied dimethyl ether solution including the component; separating the solution from the biological material; and volatilizing or separating the liquefied dimethyl ether from the solution.

3 Claims, 5 Drawing Sheets

(30) Foreign Application Priority Data

Aug. 22, 2018 (JP) .............................. JP2018-155506
Aug. 22, 2018 (JP) .............................. JP2018-155574

(58) Field of Classification Search
CPC ...... B01D 36/00; B01D 36/001; B01D 36/04;
B01D 37/00; B01D 11/02; B01D
11/0203; B01D 11/0292; A61K 2236/00;
A61K 36/87; A61K 36/28; A61K 35/44;
A61K 2236/30; A61K 2236/33; A61K
2236/331; A61K 2236/333; A61K
2236/35; A61K 2236/50; A61K 2236/51;
C11B 1/10; C11B 1/108; C11B 3/006;
C11B 7/0008; C11B 7/0025; C11B 7/005;
C11B 7/0091
See application file for complete search history.

(56) References Cited

U.S. PATENT DOCUMENTS

| | | | | |
|---|---|---|---|---|
| 6,860,998 B1* | 3/2005 | Wilde | ....................... | C11B 1/10 210/194 |
| 7,101,996 B2 | 9/2006 | Skuratowicz | | |
| 9,651,304 B1* | 5/2017 | Caulfield | ................ | F26B 5/005 |
| 2005/0283010 A1* | 12/2005 | Chordia | ............ | B01D 11/0203 422/268 |
| 2006/0275533 A1* | 12/2006 | Fletcher | ............. | B01D 11/0284 426/426 |
| 2009/0166175 A1* | 7/2009 | Waibel | ................. | B01D 11/028 202/185.1 |
| 2010/0151098 A1* | 6/2010 | Catchpole | .......... | B01D 11/0292 426/425 |
| 2010/0160659 A1 | 6/2010 | Catchpole et al. | | |
| 2013/0046105 A1* | 2/2013 | Avgousti | ................ | A23K 40/25 554/165 |
| 2013/0167432 A1* | 7/2013 | Kale | ....................... | C11B 1/108 44/403 |
| 2015/0072943 A1* | 3/2015 | Croci | ................... | A61K 31/739 514/25 |
| 2016/0228483 A1* | 8/2016 | Cox | ...................... | C07D 489/02 |
| 2016/0331699 A1* | 11/2016 | Xu | ......................... | A61K 36/71 |
| 2017/0022448 A1* | 1/2017 | Kanda | ....................... | C11B 1/10 |
| 2017/0183377 A1* | 6/2017 | Caulfield | ................ | F26B 21/14 |
| 2018/0002374 A1* | 1/2018 | Laubsch | ................. | F26B 5/005 |
| 2019/0301986 A1* | 10/2019 | Olechno | ............ | C12N 15/1003 |
| 2020/0179568 A1 | 6/2020 | Shinohara et al. | | |
| 2021/0339164 A1 | 11/2021 | Torii et al. | | |

FOREIGN PATENT DOCUMENTS

| | | | | |
|---|---|---|---|---|
| JP | 2001-106636 | | 4/2001 | |
| JP | 2001-139945 | | 5/2001 | |
| JP | 2010-240609 | | 10/2010 | |
| JP | 2018-186796 | | 11/2018 | |
| JP | 2019-154349 | | 9/2019 | |
| JP | 2020-005622 | | 1/2020 | |
| JP | 2020-006130 | | 1/2020 | |
| JP | 2020-006357 | | 1/2020 | |
| WO | WO 2004/066744 A1 | | 8/2004 | |
| WO | WO 2006058382 | * | 12/2004 | ............ B01D 11/02 |
| WO | WO 2007/136281 A1 | | 11/2007 | |
| WO | WO 2016/053678 A1 | | 4/2016 | |

OTHER PUBLICATIONS

Chinese Office Action dated Jul. 21, 2021 in Chinese Application No. 201980016232.7, with English translation, 21 pages.
International Search Report and Written Opinion dated May 24, 2019 in PCT/JP2019/010077 filed on Mar. 12, 2019.
Crapo, P., et al., "An overview of tissue and whole organ decellularization processes", Biomaterials 32, 2011, XP 55589074A, pp. 3233-3243.
Kanda, H., et al., "Extraction of Fucoxanthin from Raw Macroalgae excluding Drying and Cell Wall Disruption by Liquefied Dimethyl Ether", Marine Drugs, vol. 12, No. 5, Apr. 30, 2014, pp. 2383-2396.
U.S. Office Action dated Dec. 23, 2021 in U.S. Appl. No. 17/255,828, 8 pages.
U.S. Appl. No. 17/255,828, filed Dec. 23, 2020, 2021/0339164, Torii et al.
U.S. Office Action dated Jun. 21, 2022, in U.S. Appl. No. 17/255,828, 10 pages.
Canadian Examiner Report dated May 20, 2022 in Canadian Application No. 3,094,044, 3 pages.

* cited by examiner

| TYPE OF DENATURATION | EXTRACT IN PRESENT EMBODIMENT | EXTRACT BY HOT WATER EXTRACTION | EXTRACT BY HOT ETHANOL EXTRACTION |
|---|---|---|---|
| DISCOLORATION | ○ | × | × |
| HYDROLYSIS | ○ | × | × |
| PYROSIS | ○ | × | × |

PRESENCE/ABSENCE OF DENATURATION: ○ NONE, × DENATURED

FIG.4B

| TYPE OF DENATURATION | EXTRACTION RESIDUE IN PRESENT EMBODIMENT | EXTRACTION RESIDUE BY HOT WATER EXTRACTION | EXTRACTION RESIDUE BY HOT ETHANOL EXTRACTION |
|---|---|---|---|
| DISCOLORATION | ○ | × | × |
| HYDROLYSIS | ○ | × | × |
| PYROSIS | ○ | × | × |

PRESENCE/ABSENCE OF DENATURATION: ○ NONE, × DENATURED

|  | EXAMPLE 1 | EXAMPLE 2 | COMPARATIVE EXAMPLE 1 | COMPARATIVE EXAMPLE 2 |
|---|---|---|---|---|
| EXTRACTION MATERIAL | STEM LETTUCE | STEM LETTUCE | STEM LETTUCE | STEM LETTUCE |
| EXTRACTION SOLVENT | LIQUEFIED DIMETHYL ETHER | LIQUEFIED DIMETHYL ETHER | HEXANE | HEXANE |
| AUXILIARY SOLVENT | WATER | NONE | NONE | NONE |
| EXTRACTION TEMPERATURE | 25°C | 25°C | 25°C | 90°C |
| EXTRACTION PRESSURE | 0.70MPa | 0.70MPa | 0.10MPa | 0.10MPa |
| EXTRACTION RATIO | 4.1% BY MASS | 2.0% BY MASS | 1.3% BY MASS | 2.7% BY MASS |
| DISCOLORATION | NONE | NONE | NONE | DISCOLORED |

[Fig. 7]

|  | EXAMPLE 3 | EXAMPLE 4 | COMPARATIVE EXAMPLE 3 | COMPARATIVE EXAMPLE 4 |
|---|---|---|---|---|
| EXTRACTION MATERIAL | PIG AORTA | PIG AORTA | PIG AORTA | PIG AORTA |
| EXTRACTION SOLVENT | LIQUEFIED DIMETHYL ETHER | LIQUEFIED DIMETHYL ETHER | HEXANE | HEXANE |
| AUXILIARY SOLVENT | WATER | NONE | NONE | NONE |
| EXTRACTION TEMPERATURE | 25°C | 25°C | 25°C | 90°C |
| EXTRACTION PRESSURE | 0.70MPa | 0.70MPa | 0.10MPa | 0.10MPa |
| EXTRACTION RATIO | 3.0% BY MASS | 2.8% BY MASS | 1.0% BY MASS | 1.7% BY MASS |
| DISCOLORATION | NONE | NONE | NONE | DISCOLORED |

[Fig. 8]

|  | EXAMPLE 6 | EXAMPLE 7 | COMPARATIVE EXAMPLE 5 | COMPARATIVE EXAMPLE 6 |
|---|---|---|---|---|
| EXTRACTION MATERIAL | STEM LETTUCE | STEM LETTUCE | STEM LETTUCE | STEM LETTUCE |
| EXTRACTION SOLVENT | LIQUEFIED DIMETHYL ETHER | LIQUEFIED DIMETHYL ETHER | HEXANE | HEXANE |
| AUXILIARY SOLVENT | WATER | NONE | NONE | NONE |
| EXTRACTION TEMPERATURE | 25°C | 25°C | 25°C | 90°C |
| EXTRACTION PRESSURE | 0.70MPa | 0.70MPa | 0.10MPa | 0.10MPa |
| EXTRACTION RATIO | 4.1% BY MASS | 2.0% BY MASS | 1.3% BY MASS | 2.7% BY MASS |
| DISCOLORATION | NONE | NONE | NONE | DISCOLORED |

[Fig. 9]

|  | EXAMPLE 8 | EXAMPLE 9 | COMPARATIVE EXAMPLE 7 | COMPARATIVE EXAMPLE 8 |
|---|---|---|---|---|
| EXTRACTION MATERIAL | PIG AORTA | PIG AORTA | PIG AORTA | PIG AORTA |
| EXTRACTION SOLVENT | LIQUEFIED DIMETHYL ETHER | LIQUEFIED DIMETHYL ETHER | HEXANE | HEXANE |
| AUXILIARY SOLVENT | WATER | NONE | NONE | NONE |
| EXTRACTION TEMPERATURE | 25°C | 25°C | 25°C | 90°C |
| EXTRACTION PRESSURE | 0.70MPa | 0.70MPa | 0.10MPa | 0.10MPa |
| EXTRACTION RATIO | 3.0% BY MASS | 2.8% BY MASS | 1.0% BY MASS | 1.7% BY MASS |
| DISCOLORATION | NONE | NONE | NONE | DISCOLORED |

METHOD OF PRODUCING EXTRACT AND EXTRACTION RESIDUE OF BIOLOGICAL MATERIAL, EXTRACT, AND EXTRACTION RESIDUE

TECHNICAL FIELD

The present invention relates to a method of producing an extract and an extraction residue of a biological material, an extract, and an extraction residue.

BACKGROUND ART

Conventionally, an extraction method using liquefied dimethyl ether as an extraction solvent is proposed in PTL 1. According to the disclosure of PTL 1, liquefied dimethyl ether in which the saturation amount of water is dissolved is contacted with a target material containing moisture and oil to produce a mixture of liquefied dimethyl ether and oil and the deoiled target material.

The use of dimethyl ether as an extraction solvent in producing an extract of a plant material is proposed in PTL 2. According to the disclosure of PTL 2, an extraction liquid obtained by contacting dimethyl ether with a plant material is separated into a dimethyl ether layer and an aqueous layer, and after removing the aqueous layer, the dimethyl ether layer is evaporated and dried to produce an extract.

SUMMARY OF INVENTION

Technical Problem

Unfortunately, the extraction method disclosed in PTL 1 has the following problem because of the use of liquefied dimethyl ether having the saturation amount of moisture dissolved therein. That is, liquefied dimethyl ether having the saturation amount of moisture dissolved therein is contacted with a plant material, so that moisture or a water-soluble compound in the plant material is not dissolved in the liquefied dimethyl ether. As a result, a plant-derived moisture or water-soluble compound is unable to be extracted.

In the production method disclosed in PTL 2, since the dimethyl ether layer is evaporated and dried after removal of the aqueous layer, a plant-derived water-soluble natural component is removed together with the aqueous layer, and an extract containing a water-soluble natural component is unable to be produced. It is therefore difficult to provide a water-soluble natural component.

In view of the situation above, there is a need to provide a method of producing an extract and an extraction residue of a biological material that is capable of extracting a plant or other biologically derived moisture and water-soluble compound satisfactorily, and to provide an extract and an extraction residue that can provide a plant or other biologically derived water-soluble natural component.

Solution to Problem

According to an embodiment, a method of producing an extract of an animal-derived or plant-derived biological material, that includes extracting a component in the biological material using liquefied dimethyl ether for the biological material to obtain a liquefied dimethyl ether solution including the component; separating the solution from the biological material; and volatilizing or separating the liquefied dimethyl ether from the solution.

Advantageous Effects of Invention

According to the embodiment, in the extraction process, liquefied dimethyl ether including an auxiliary solvent in an amount equal to or less than the saturation amount is contacted with a biological material to obtain a liquid mixture in which components such as moisture, a water-soluble compound, and a lipid-soluble compound in the biological material is transported from the biological material to the liquefied dimethyl ether. In the separation process, the liquid mixture is separated from the biological material. In the extract concentration process, liquefied dimethyl ether is evaporated and separated from the liquid mixture to obtain an extract. Thus, biologically derived moisture and water-soluble compound can be well extracted. In the extraction residue producing process, the extraction residue is obtained by evaporating and separating liquefied dimethyl ether from the biological material. Thus, an extraction residue from which moisture and the extract are well removed can be obtained.

The present invention also provides a water-soluble natural component since the extract contains a water-soluble or lipid-soluble natural component and is not denatured by pyrosis.

DESCRIPTION OF EMBODIMENTS

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

Preferred embodiments of a method of producing an extract and an extraction residue of a biological material, and an extract and an extraction residue of biological tissue according to the present invention will be described in detail below with reference to the accompanying drawings. The biological material means a material derived from any one of plants with cells having cell walls, fungi, archaebacteria, eubacteria, or animals with cells having no cell walls. In the case of a plant-derived material, the biological material is a material derived from at least one of leaves, branches, trees, petals, stems, roots, fruits, pericarps, and seeds. In the case of an animal-derived material, the biological material is an animal-derived material that is at least one of, for example, human or other mammal-derived soft tissue including skin, blood vessel, heart valve, cornea, amnion, and dura mater, or part thereof, organs including heart, kidney, liver, pancreas, and brain, or part thereof, bone, cartilage, and tendon, or part thereof. The biological tissue means tissue derived from any of plants having cell walls, fungi, archaebacteria, eubacteria, or animals having no cell walls.

Figure 1:
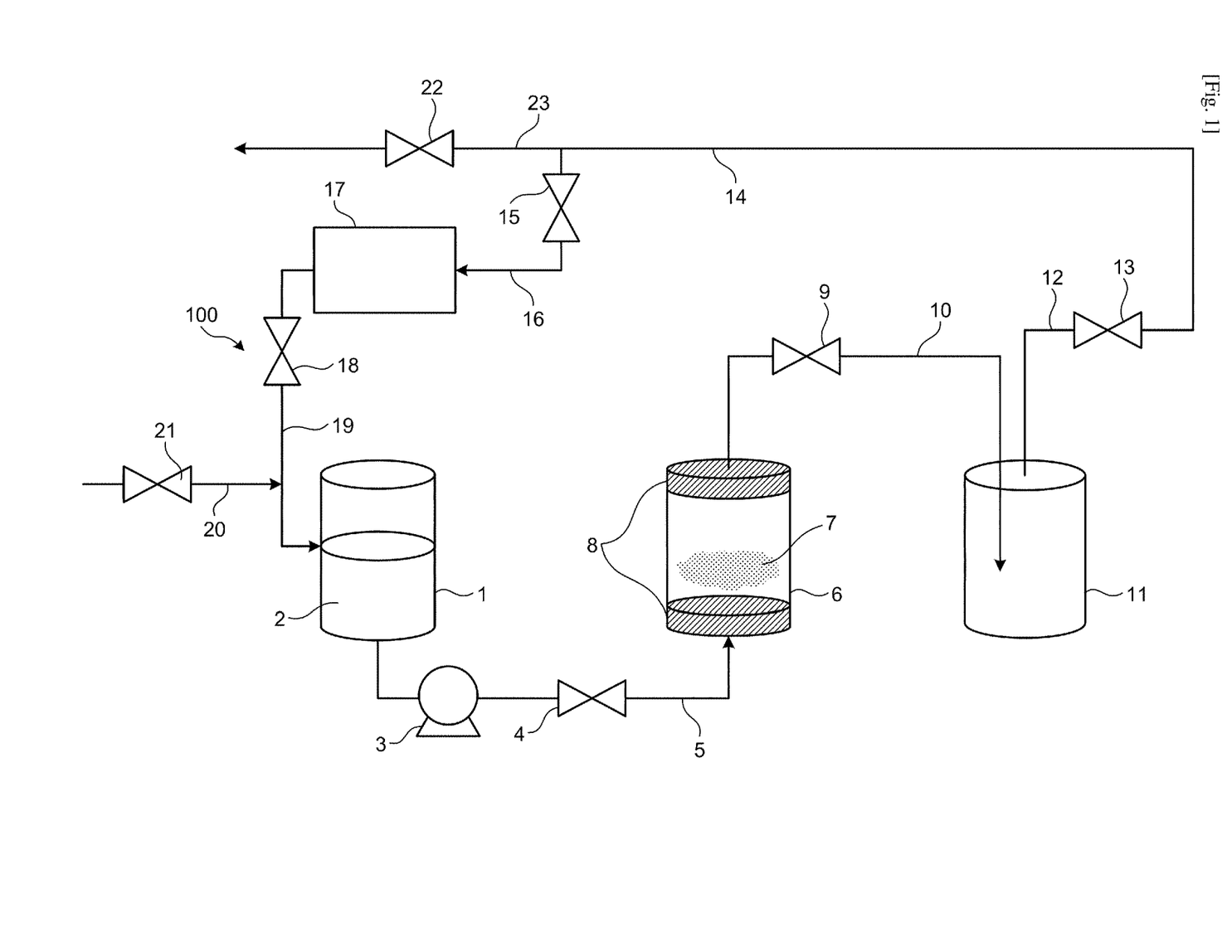
FIG. 1 is a diagram illustrating an exemplary extraction apparatus according to the present embodiment.

FIG. 1 illustrates an exemplary extraction apparatus according to the present embodiment. The extraction apparatus is an apparatus for producing an extract and an extraction residue of biological tissue by performing a method of producing an extract and an extraction residue of a biological material. FIG. 1 merely illustrates the shape, dimensions, and arrangement of components to an extent that helps the understanding of the extraction apparatus.

The extraction apparatus 100 includes a storage tank 1 for storing liquefied dimethyl ether 2 including an auxiliary solvent in an amount equal to or less than the saturation amount (hereinafter simply referred to as liquefied dimethyl ether), an extraction tank 6 for contacting a biological material 7 with liquefied dimethyl ether 2, a separation tank 11 for separating a liquid drained from the extraction tank 6, and a pump 3 for sending liquefied dimethyl ether 2 from the storage tank 1 to the extraction tank 6.

The liquefied dimethyl ether 2 stored in the storage tank 1 is prepared by bringing dimethyl ether to a saturation vapor pressure or higher to achieve a liquid state and preferably includes an auxiliary solvent such as water or alcohol in an amount equal to or less than the saturation amount. Here, the amount of auxiliary solvent added is preferably equal to or less than the saturation amount in the liquefied dimethyl ether, more specifically, preferably equal to or less than 7% by mass relative to the liquefied dimethyl ether 2. The addition of an auxiliary solvent can change the solvent characteristics such as solubility and polarity of the liquefied dimethyl ether.

The extraction apparatus 100 includes conduits 5, 10, 12, 14, 16, 19, 20, and 23 for feeding or draining the liquefied dimethyl ether 2 and valves 4, 9, 13, 15, 18, 21, and 22 for regulating the pressure in each tank to control feeding and drainage of the liquefied dimethyl ether 2. The extraction tank 6 and the separation tank 11 can regulate the temperature at 1 to 40° C. and regulate the pressure at 0.2 to 5 MPa in order to maintain the liquid state of the liquefied dimethyl ether 2.

In the extraction apparatus 100 above, the pump 3, the valve 4, and the conduit 5 function as a feeding unit for feeding the liquefied dimethyl ether 2 from the storage tank 1 to the extraction tank 6. The extraction tank 6 functions as a contacting unit. The conduit 10 and the valve 9 for draining the liquefied dimethyl ether 2 from the extraction tank 6 functions as a draining unit. The separation tank 11 functions as a separating unit. The condenser 17 connected to the conduit 16 functions as a condensing unit. The conduit 12 and the valve 13 connected to the separation tank 11 function as a vaporizing unit. The storage tank 1 functions as a storing unit. The conduits 19 and 20 function as a supply unit.

The extraction apparatus 100 further includes optional components such as a thermometer and a pressure gauge that detect temperature and pressure in each tank, a stirrer for stirring in each tank, and a device that circulates an inert gas such as nitrogen for purging an active gas such as oxygen in the tanks and the conduits.

Figure 2:
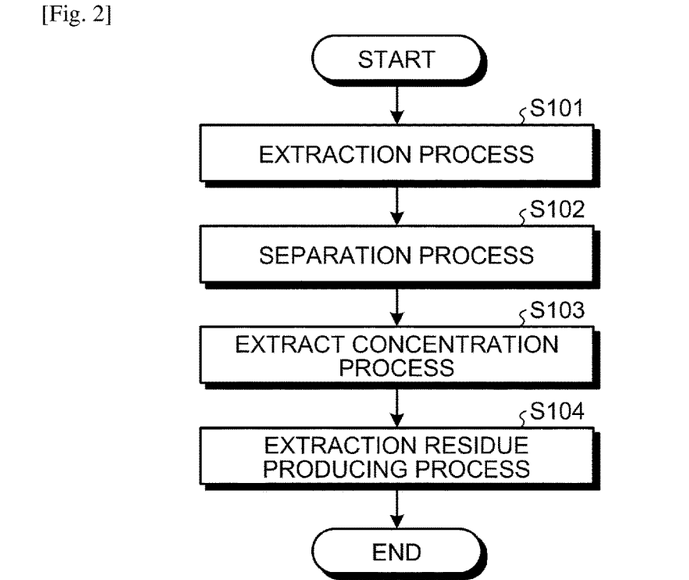
FIG. 2 is a flowchart illustrating an example of a method of producing an extract and an extraction residue of a biological material in the present embodiment.

FIG. 2 is a flowchart illustrating an example of the method of producing an extract and an extraction residue of a biological material in the present embodiment.

As illustrated in FIG. 2, the method of producing an extract and an extraction residue of a biological material includes an extraction process (step S101), a separation process (step S102), an extract concentration process (step S103), and an extraction residue producing process (step S104).

In the following, the processes of the method of producing an extract extracted from a biological material and an extraction residue are described with reference to the operation in the extraction apparatus 100.

First of all, a biological material is fed into the extraction tank 6 with filters 8 installed on the upstream side and the downstream side. Here, the valves 4, 9, 13, 15, 18, 21, and 22 are in a closed state. When liquefied dimethyl ether 2 is not stored sufficiently in the storage tank 1, the valve 21 is opened, and the liquefied dimethyl ether 2 is supplied to the storage tank 1 via the conduit 20. The valve 21 is thereafter closed.

In the extraction process (step S101), the liquefied dimethyl ether 2 including an auxiliary solvent (water or alcohol) in an amount equal to or less than the saturation amount is contacted with a material 7 to transport water, a water-soluble compound, and a lipid-soluble compound contained in the material 7 to the liquefied dimethyl ether 2 to obtain a liquid mixture. Water means moisture contained in the raw material. Such an extraction process (step S101) is performed as follows.

The valve 4 in the extraction apparatus 100 is opened, and the liquefied dimethyl ether 2 in the storage tank 1 is drained by the pump 3 and fed into the extraction tank 6 via the conduit 5 until coming into contact with the material 7. The valve 4 is thereafter closed.

This process yields a liquid mixture in which in the case of a plant material, water and a water-soluble compound or a lipid-soluble compound such as an aromatic compound, a natural pigment compound, an antioxidant compound, an antibacterial compound, and an antiviral compound are transported as material-derived components to the liquefied dimethyl ether 2. In the case of animal cells, a liquid mixture is obtained, in which water, a water-soluble compound such as water-soluble vitamin, water-soluble protein, and water-soluble plant fiber, and a lipid-soluble compound such as lipid and fat-soluble vitamin is transported to the liquefied dimethyl ether.

In the separation process (step S102), the liquid mixture is separated from the material 7. This separation process (step S102) is performed as follows.

The valves 4 and 9 in the extraction apparatus 100 are opened, and the liquefied dimethyl ether 2 is fed by the pump 3 from the storage tank 1 into the extraction tank 6 via the conduit 5. Then, the liquid mixture in the extraction tank 6 is fed into the separation tank 11 via the conduit 10. That is, when new liquefied dimethyl ether is drained from the storage tank 1 into the extraction tank 6, the liquid mixture in the extraction tank 6 is pushed into the separation tank 11. As a result, the inside of the extraction tank 6 is replaced by new liquefied dimethyl ether. On the other hand, the material 7 in the extraction tank 6 stays in the extraction tank 6 because of the filters 8 on the upstream side and the downstream side of the extraction tank 6. That is, new liquefied dimethyl ether is fed into the extraction tank 6, whereby the liquid mixture is pushed out of the extraction tank 6 and separated from the material 7.

The valves 4 and 9 are opened at a timing after a sufficient time for transporting water and the like contained in the material 7 to liquefied dimethyl ether 2 elapses after liquefied dimethyl ether 2 is fed into the extraction tank 6. Here, liquefied dimethyl ether 2 may be left in contact with the material 7 for a predetermined time or may be stirred.

In the extract concentration process (step S103), liquefied dimethyl ether is evaporated and separated from the liquid mixture to obtain an extract. In the extraction residue producing process (step S104), liquefied dimethyl ether is evaporated and separated from the material 7 to obtain an extraction residue. The extract concentration process (step S103) and the extraction residue producing process (step S104) are performed as follows.

In the extraction apparatus 100, when the valve 4 is closed and the valves 9, 13, and 22 are opened, the path from the valve 4 to the valve 13 attains a pressure lower than the saturation vapor pressure of dimethyl ether. As a result, the liquefied dimethyl ether 2 in this path is vaporized and discharged from the conduit 23 via the conduit 14. Here, dimethyl ether may be discharged using the pump 3, as necessary.

In the separation tank 11, the liquefied dimethyl ether 2 evaporates and separates from the liquid mixture, so that the liquefied dimethyl ether solution including the extract is concentrated, resulting in an extract. In the extraction tank 6, the extraction residue of the material 7 is produced.

The evaporation and separation operation for liquefied dimethyl ether 2 may be performed with the valve 9 kept closed. With the liquefied dimethyl ether 2 kept contact with the material 7 in the extraction tank 6, dimethyl ether in the path following the valve 9 is discharged. As a result, in the separation tank 11, an extract is produced in which liquefied dimethyl ether 2 evaporates and separates from the liquid mixture. The method of producing an extract and an extraction residue of the material described above may include a process of condensing the liquefied dimethyl ether separated in the extract concentration process (step S103) and the extraction residue producing process (step S104).

In this case, the valve 22 is closed and the valve 15 is opened in the extraction apparatus 100, whereby the vaporized dimethyl ether is fed into the condenser 17 via the conduit 16. As a result, the fed dimethyl ether is condensed in the condenser 17 to produce liquefied dimethyl ether 2. With the valve 18 opened, the produced liquefied dimethyl ether 2 is fed into the storage tank 1 via the conduit 19, so that the liquefied dimethyl ether 2 can be reused.

In the description above, the liquefied dimethyl ether 2 in the storage tank 1 is discontinuously drained. However, the liquefied dimethyl ether 2 in the storage tank 1 may be continuously drained.

With the valves 4 and 9 opened, the liquefied dimethyl ether 2 in the storage tank 1 may be continuously fed from the storage tank 1 to the extraction tank 6 via the conduit 5, and the liquid mixture in the extraction tank 6 may be continuously drained to the separation tank 11 via the conduit 10. In this case, it is preferable that the extraction tank 6 is configured such that the liquefied dimethyl ether 2 is continuously in contact with the material 7.

The extraction apparatus 100 changes the gas-liquid state of dimethyl ether by changing the pressure in the apparatus. However, the gas-liquid state may be changed by temperature change, rather than pressure change.

The extraction residue produced from an animal-derived material by the extraction apparatus 100 may be used as a regenerative medical material by removing nucleic acids. For example, extraction using pig skin as a raw material by the extraction apparatus 100 is described. First of all, an extraction residue produced from pig skin is contacted with liquefied dimethyl ether. Then, phospholipid which is a main component of the cell membrane is dissolved. As a result, the cells of biological tissue are destroyed, and the pig skin in which the nucleic acids in the cells are exposed outside the cells is produced as an extraction residue. A solution including a nuclease is contacted with the extraction residue to decompose the nucleic acids exposed outside the cells. Subsequently, the extraction residue with the nucleic acids decomposed is contacted with a cleaning liquid to completely wash away the remaining nucleic acids or a decomposition product, resulting in an extraction residue free from nucleic acids.

The nuclease may be any nuclease that can decompose DNA and examples include DNase (for example, DNaseI).

The destroyed cells may be contacted with a solution including a nuclease, for example, but not limited to, by mixing and stirring a solution including a nuclease and the extraction residue with the destroyed cells, or by dipping the extraction residue with the destroyed cells in a solution including a nuclease, or by contacting a solution including a nuclease with the extraction residue with the destroyed cells.

The method of contacting a solution including a nuclease with the destroyed cells can be selected as appropriate according to the property of the extraction residue with the destroyed cells.

Examples of the cleaning liquid include water, a physiologically adaptive liquid, an aqueous solution of a physiologically acceptable organic solvent, and a liquid including liquid gas.

Examples of the physiologically adaptive liquid include, but not limited to, physiological saline and phosphate buffered saline (PBS), and two or more may be used in combination. Among those, physiological saline is preferred.

Examples of the physiologically acceptable organic solvent include, but not limited to, ethanol because of its low biological toxicity.

The liquid including liquid gas may be a liquid including liquefied dimethyl ether or may be a liquid including different liquid gases.

The extraction residue with the decomposed nucleic acids may be contacted with a cleaning liquid, for example, but not limited to, by mixing and stirring a cleaning liquid and the extraction residue with the decomposed nucleic acid components, by dipping the extraction residue with the decomposed nucleic acids in a cleaning liquid, or by contacting a cleaning liquid with the extraction residue with the decomposed nucleic acid components.

The method of contacting the extraction residue with the decomposed nucleic acids with a cleaning liquid can be selected as appropriate according to the property of the extraction residue with the decomposed nucleic acids.

The extraction residue with the decomposed nucleic acids is washed with a cleaning liquid, preferably, at a temperature between 4° C. and 40° C. This is because at a temperature lower than 4° C., cell tissue that is the extraction residue may be damaged due to freeze of moisture, and at a temperature higher than 40° C., protein of the cell tissue that is the extraction residue may be denatured and damaged.

When the extraction residue with the decomposed nucleic acids is washed with a liquid including liquid gas, the washing is preferably performed under an environment equal to or higher than the saturation vapor pressure, for example, in the extraction tank in a sealed state in order to keep the liquid state of the liquid gas.

The extraction residue with the decomposed nucleic acids is washed with a cleaning liquid for a time by which nuclease, nucleic acids, and nucleic acid-decomposed products can be sufficiently removed.

When the extraction residue with the decomposed nucleic acids is washed with a cleaning liquid, cleaning may be repeated by changing the cleaning liquid. The repeated washing can increase the cleaning efficiency.

The processes above yield decellularized tissue as an extraction residue of an animal-derived material with substantially no damage and with a DNA content per dry mass of less than 50 ng/mg. When the DNA content per dry mass of decellularized tissue is less than 50 ng/mg, immune reactions in in-vivo transplantation can be avoided (NPL 1: Biomaterials 32 (2011) 3233-3243).

Extract and Extraction Residue Produced from Material Having Cell Walls

The extraction apparatus 100 can produce an extract and an extraction residue of a plant-derived material 7 as follows.

First of all, a plant material 7 that is at least one of leaves, branches, trees, petals, stems, roots, fruits, pericarps, and seeds is fed into the extraction tank 6 with filters 8 installed on the upstream side and the downstream side. Here, the valves 4, 9, 13, 15, 18, 21, and 22 are in a closed state. When liquefied dimethyl ether 2 is not stored sufficiently in the storage tank 1, the valve 21 is opened and liquefied dimethyl ether 2 is supplied to the storage tank 1 via the conduit 20. The valve 21 is thereafter closed. Here, when the valve 21 is opened, the valve 18 may be opened, and when the valve 21 is closed, the valve 18 may be closed.

Subsequently, the valve 4 is opened, and the liquefied dimethyl ether 2 in the storage tank 1 is drained by the pump 3 and fed into the extraction tank 6 via the conduit 5 until coming into contact with the plant material 7. The valve 4 is thereafter closed.

When the material 7 is dipped in liquefied dimethyl ether 2 in the extraction tank 6, water and a water-soluble compound or a lipid-soluble compound including at least one of an aromatic compound, a natural pigment compound, an antioxidant compound, an antibacterial compound, and an antiviral compound, contained in the material 7 are extracted from the plant-derived material 7 by the liquefied dimethyl ether 2. As a result, a liquid mixture is obtained, in which water, a water-soluble compound, and a lipid-soluble compound in the plant-derived material 7 are dissolved in liquefied dimethyl ether 2. Water means moisture included in the material.

With the valves 4 and 9 opened, the liquefied dimethyl ether 2 is fed by the pump 3 from the storage tank 1 into the extraction tank 6 via the conduit 5. Then, the liquid mixture in the extraction tank 6 is fed into the separation tank 11 via the conduit 10. That is, when new liquefied dimethyl ether is drained from the storage tank 1 into the extraction tank 6, the liquid mixture in the extraction tank 6 is pushed into the separation tank 11. As a result, the inside of the extraction tank 6 is replaced by new liquefied dimethyl ether, and the plant-derived material 7 in the extraction tank 6 stays in the extraction tank 6 because the extraction tank 6 has filters 8 on the upstream side and the downstream side. That is, new liquefied dimethyl ether is fed into the extraction tank 6, whereby the liquid mixture is pushed out of the extraction tank 6 and separated from the plant-derived material 7.

The valves 4 and 9 are opened at a timing after a sufficient time for transporting moisture and the like in the plant material 7 to the liquefied dimethyl ether 2 elapses after the liquefied dimethyl ether 2 is fed into the extraction tank 6. Here, the liquefied dimethyl ether 2 may be left in contact with the plant material 7 for a predetermined time or may be stirred.

Subsequently, with the valve 4 closed and the valves 9, 13, and 22 opened, the inside of the path from the valve 4 to the valve 13 attains a pressure lower than the saturation vapor pressure of dimethyl ether. Then, the liquefied dimethyl ether 2 in this path is vaporized and discharged from the conduit 23 via the conduit 14. In this case, the pump 3 may be used as necessary to discharge dimethyl ether.

In the separation tank 11, an extract is produced in which the liquefied dimethyl ether 2 vaporizes and separates from the liquid mixture, and in the extraction tank 6, an extraction residue of the plant-derived material 7 is produced.

In the case described above, the valve 22 is opened and the valve 15 is closed. However, the valve 22 may be closed and the valve 15 may be opened. By doing so, the vaporized dimethyl ether is fed into the condenser 17 via the conduit 16. As a result, in the condenser 17, the fed dimethyl ether is condensed to produce liquefied dimethyl ether 2. With the valve 18 opened, the produced liquefied dimethyl ether 2 is fed into the storage tank 1 via the conduit 19 and can be reused as liquefied dimethyl ether 2.

In the present embodiment above, the material is a plant-derived material. However, materials derived from fungi such as mushrooms or molds, archaebacteria, or eubacteria, having cell walls like plants can be used instead of plants.

Extract and Extraction Residue Produced from Material Having No Cell Walls

In the extraction apparatus 100 above, an extract and an extraction residue can be produced from an animal-derived material 7 as follows.

First of all, an animal-derived material 7 that is at least one of human or other mammal-derived soft tissue including skin, blood vessel, heart valve, cornea, amnion, and dura mater, organs including heart, kidney, liver, pancreas, and brain, bone, cartilage, tendon, or part thereof is fed into the extraction tank 6 with filters 8 installed on the upstream side and the downstream side. Here, the valves 4, 9, 13, 15, 18, 21, and 22 are in a closed state. When liquefied dimethyl ether 2 is not stored sufficiently in the storage tank 1, the valve 21 is opened and liquefied dimethyl ether 2 is supplied to the storage tank 1 via the conduit 20. The valve 21 is thereafter closed. Here, when the valve 21 is opened, the valve 18 may be opened, and when the valve 21 is closed, the valve 18 may be closed.

Subsequently, the valve 4 is opened, and the liquefied dimethyl ether 2 in the storage tank 1 is drained by the pump 3 and fed into the extraction tank 6 via the conduit 5 until coming into contact with the animal-derived material 7. The valve 4 is thereafter closed.

When the animal-derived material 7 is dipped in liquefied dimethyl ether 2 in the extraction tank 6, water, a water-soluble compound such as water-soluble vitamin, water-soluble protein, and water-soluble plant fiber, and a lipid-soluble compound such as lipid and fat-soluble vitamin in the animal-derived material 7 are extracted from the animal-derived material 7 by the liquefied dimethyl ether 2. As a result, a liquid mixture is obtained in which water, a water-soluble compound, and a lipid-soluble compound in the animal-derived material 7 are dissolved in the liquefied dimethyl ether 2. Water means moisture included in the material.

The valves 4 and 9 are opened at a timing after a sufficient time for transporting water and the like in the animal-derived material 7 to the liquefied dimethyl ether 2 elapses after the liquefied dimethyl ether 2 is fed into the extraction tank 6. Here, the liquefied dimethyl ether 2 may be left in contact with the animal-derived material 7 for a predetermined time or may be stirred.

Subsequently, with the valve 4 closed and the valves 9, 13, and 22 opened, the inside of the path from the valve 4 to the valve 13 attains a pressure lower than the saturation vapor pressure of dimethyl ether. Then, the liquefied dimethyl ether 2 in this path is vaporized and discharged from the conduit 23 via the conduit 14. Here, the pump 3 may be used as necessary to discharge dimethyl ether.

Subsequently, with the valve 4 closed and the valves 9, 13, and 22 opened, the inside of the path from the valve 4 to the valve 13 attains a pressure lower than the saturation vapor pressure of dimethyl ether. Then, the liquefied dimethyl ether 2 in this path is vaporized and discharged from the conduit 23 via the conduit 14. Here, the pump 3 may be used as necessary to discharge dimethyl ether.

In the separation tank 11, an extract is produced in which the liquefied dimethyl ether 2 is evaporated and separated from the liquid mixture, and in the extraction tank 6, an extraction residue of the animal-derived material 7 is produced.

In the case above, the valve 22 is opened and the valve 15 is closed. However, the valve 22 may be closed and the valve 15 may be opened. In this manner, the vaporized dimethyl ether is fed into the condenser 17 via the conduit 16. As a result, in the condenser 17, the fed dimethyl ether is condensed to produce liquefied dimethyl ether 2. With the valve 18 opened, the produced liquefied dimethyl ether 2 is fed into the storage tank 1 via the conduit 19 and can be reused as liquefied dimethyl ether 2.

In the description above, the liquefied dimethyl ether 2 in the storage tank 1 is discontinuously drained. However, the liquefied dimethyl ether 2 may be continuously drained as follows.

With the valves 4 and 9 opened, the liquefied dimethyl ether 2 in the storage tank 1 may be continuously fed into the extraction tank 6 from the storage tank 1 via the conduit 5, and the liquid mixture in the extraction tank 6 may be continuously drained to the separation tank 11 via the conduit 10. In this case, it is preferable that the liquefied dimethyl ether 2 is continuously in contact with the material 7.

The extraction apparatus 100 changes the gas-liquid state of dimethyl ether by changing the pressure in the tank. However, the gas-liquid state may be changed by temperature change, rather than by pressure change.

Figure 3:
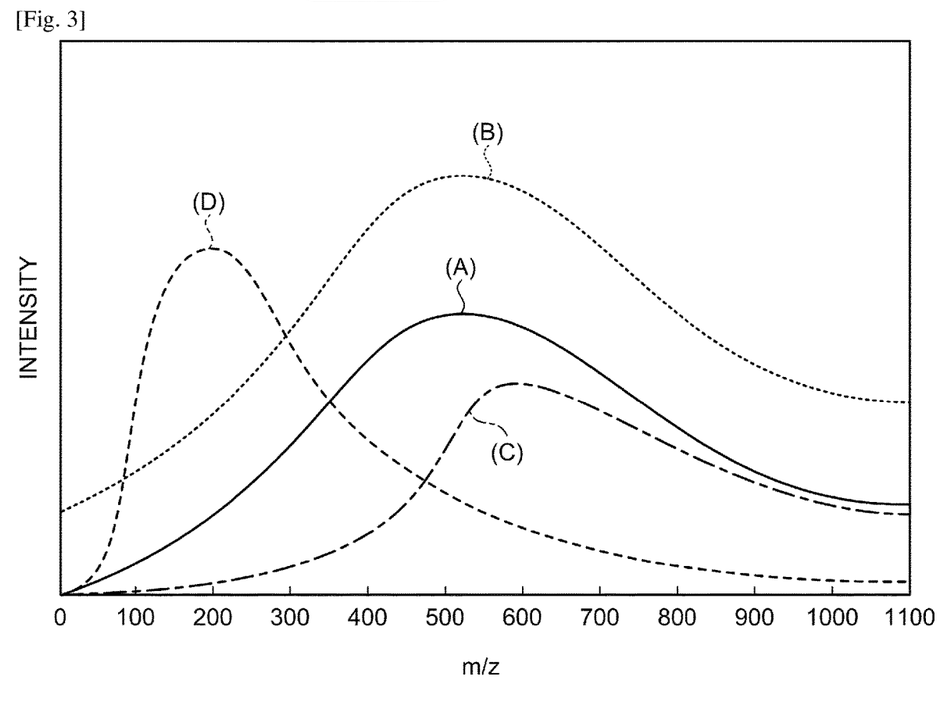
FIG. 3 is a graph illustrating the result of mass spectrum obtained by mass spectrometry of the extract produced by the extraction apparatus illustrated in FIG. 1.

The material-derived extract produced in the separation tank 11 by the extraction apparatus 100 was analyzed by a mass spectrometer, and the result is shown in FIG. 3. In FIG. 3, (A) illustrates the analysis result of the extract produced by the extraction apparatus 100. (B) illustrates the theoretical amount derived from the material. (C) illustrates the analysis result of the extract produced by a conventional method of removing the aqueous layer and evaporating the dimethyl ether layer to dryness after separating the dimethyl ether layer and the aqueous layer. (D) illustrates the analysis result of the extract generated by steam distillation.

It is understood from FIG. 3 that the extract (A) produced by the extraction apparatus 100 contains components of a wide range of molecular weights, similar to the theoretical amount (B). Based on this, it is understood that the extract produced by the extraction apparatus 100 includes a wide range of compounds from low-molecular-weight water-soluble compounds to high-molecular-weight lipid-soluble compounds.

More specifically, the extract (A) extracted by the extraction apparatus 100 contains a water-soluble compound or a lipid-soluble compound that is at least one of aromatic compounds, natural pigment compounds, antioxidant compounds, antibacterial compounds, and antiviral compounds, and these compounds also include a compound of a molecular weight equal to or greater than 800 g/mol. If at least one of the compounds above is extracted, the compound can be used for applications and products suitable for its characteristics. For example, an aromatic compound can be used for cosmetics, a natural pigment compound can be used for cosmetics or food additives, an antioxidant compound can be used for dietary supplements, an antibacterial compound can be used for antibacterial agents, and an antiviral compound can be used for antiviral agents.

On the other hand, the extract (C) is produced from the dimethyl ether layer from which the aqueous layer has been removed, and a low-molecular water-soluble compound is removed with the aqueous layer. Consequently, the extract has an unbalanced composition such that the low-molecular water-soluble compound content is low and the high-molecular-weight compound content is high. The extract (D) as a whole has a large amount of low-molecular-weight compound since the high-molecular-weight lipid-soluble compound is destroyed by pyrosis.

In this way, the extract produced from a biologically derived material in the present embodiment contains a water-soluble compound or a lipid-soluble compound derived from the material, and (A) has a molecular weight distribution closer to (B), compared with (D) and (C). The reason why (A) has an intensity lower than (B) is presumably that part of the material-containing component unable to be extracted by the extraction apparatus 100 remains in the extraction residue.

Figure 4A:
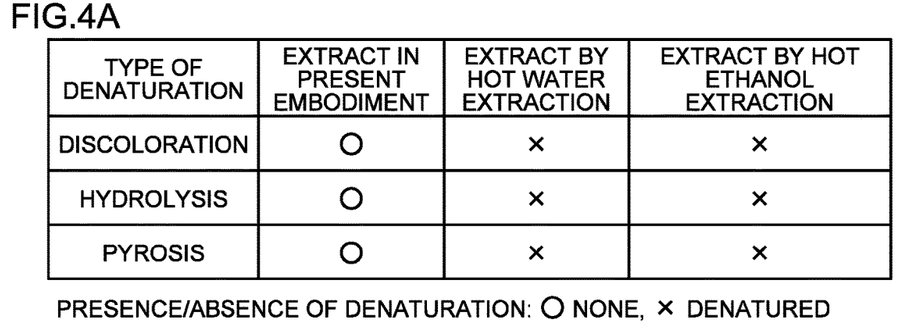
FIG. 4A is a table illustrating classification of denaturation of extracts.
Figure 4B:
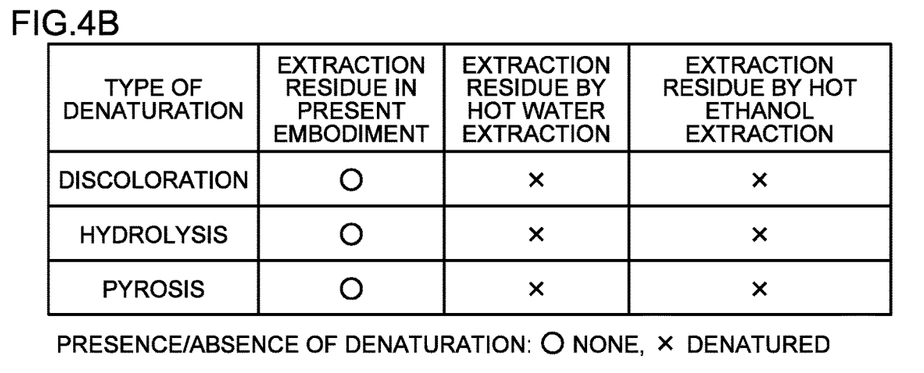
FIG. 4B is a graph illustrating classification of denaturation of extraction residues.

FIG. 4A is a table displaying classification of denaturation of extracts. FIG. 4B is a table displaying classification of denaturation of extraction residues. In FIG. 4A, the extract according to the present embodiment is produced by the extraction apparatus 100 and taken out from the separation tank 11. The extract by hot water extraction/hot ethanol extraction refers to an extract produced by, for example, an extraction method involving heating at 100° C.

The discoloration in is admixed with FIGS. 4(A) and 4(b). 4A refers to a color change of an extract or an extraction residue by an extraction operation, by visual comparison. Stem lettuce, which is green before extraction, was used as a plant-derived material. The extract extracted from stem lettuce by the extraction apparatus 100 was green, whereas the extract extracted from stem lettuce by hot water extraction/hot ethanol extraction was brown. Also in the extraction residues, the extraction residue produced by the extraction apparatus 100 was green, whereas the extraction residue produced by hot water extraction/hot ethanol extraction was brown. This may be because chlorophyll which is a pigment exhibiting green was decomposed by heating. When pig meat was used as an animal-derived material, the extract extracted from pig meat by the extraction apparatus 100 was transparent, whereas the extract extracted by hot water extraction/hot ethanol extraction was whitish. Also in the extraction residues, the extraction residue produced by the extraction apparatus 100 was white, whereas the extraction residue produced by hot water extraction/hot ethanol extraction was light brown. This may be because the protein in pig meat was heat-denatured by heating. Based on these, it is understood that the extract and the extraction residue are not discolored during extraction in the extraction apparatus 100.

Hydrolysis in FIG. 4A indicates the presence/absence of hydrolysis of a material easily hydrolyzed, such as saccharides or esters included in the material. For accurate evaluation of hydrolysis, 10 mg of sucrose alone was put into an extraction solvent (liquefied dimethyl ether, water, ethanol) and held for 2 hours under predetermined conditions (liquefied dimethyl ether: 25° C., 0.7 MPa, water/ethanol: 100° C., 0.1 MPa). Thereafter, the amount of produced glucose was measured by liquid chromatography and compared. Sucrose is easily hydrolyzed and, when hydrolyzed, produces glucose as a hydrolyzed product. Glucose was not detected in the extract extracted by the extraction apparatus 100, whereas glucose was detected from the extract extracted by hot water extraction/hot ethanol extraction. Sucrose is one of saccharides likely to be contained both in plant-derived materials and animal-derived materials, and that sucrose is not hydrolyzed indicates that hydrolysis of the extract does not occur in the extraction apparatus 100.

Hydrolysis in FIG. 4B indicates the presence/absence of hydrolysis using cellulose instead of sucrose. Cellulose is one of main components of plant cell walls and is a substance that is one of main components of the extraction residue in the case of extraction from a plant-derived material. In an extraction solvent (liquefied dimethyl ether, water, ethanol), 10 mg of cellulose alone was put and held for 2 hours under predetermined conditions (liquefied dimethyl ether: 25° C., 0.7 MPa, water/ethanol: 100° C., 0.1 MPa). Thereafter, the amount of produced glucose was measured by liquid chromatography and compared. Glucose which is a hydrolyzed product of cellulose was not detected in the extract extracted by the extraction apparatus 100, whereas glucose was detected from the extract extracted by hot water extraction/hot ethanol extraction. Based on this, it is understood that hydrolysis of the extraction residue does not occur during extraction in the extraction apparatus 100.

Pyrosis FIG. 4A indicates the presence/absence of pyrosis of an easily pyrolyzed substance included in the material. For accurate evaluation of pyrosis, 10 mg of flavonoid, kaempherol alone was put into an extraction solvent (liquefied dimethyl ether, water, ethanol) and held for 2 hours under predetermined conditions (liquefied dimethyl ether: 25° C., 0.7 MPa, water/ethanol: 100° C., 0.1 MPa). Thereafter, the amount of kaempherol in the extract was measured by liquid chromatography and the recovery ratio of kaempherol was compared. Kaempherol is a substance easily decomposed by heat. In the extract extracted by the extraction apparatus 100, the recovery ratio of kaempherol is 92%, whereas the kaempherol recovery ratio from the extract extracted by hot water extraction is 55%, and the kaempherol recovery ratio from the extract extracted by hot ethanol extraction is 65%. Based on this, it is understood that pyrosis of the extract does not occur during extraction in the extraction apparatus 100.

Pyrosis in FIG. 4B indicates the presence/absence of pyrosis using lignin instead of kaempherol. Lignin is one of main components of plant cell walls and is a substance that is one of main components of the extraction residue in the case of extraction from a plant-derived material. In an extraction solvent (liquefied dimethyl ether, water, ethanol), 1 g of lignin alone was put and held for 2 hours under predetermined conditions (liquefied dimethyl ether: 25° C., 0.7 MPa, water/ethanol: 100° C., 0.1 MPa). Thereafter, the extract was washed and filtered, the weight of lignin obtained as the extraction residue was measured, and the recovery ratio of lignin was compared. The recovery ratio of lignin in the extraction residue produced by the extraction apparatus 100 is 98%, whereas the lignin recovery ratio of the extraction residue produced by the hot water extraction is 86%, and the lignin recovery ratio of the extraction residue produced by hot ethanol extraction is 84%. Based on this, it is understood that pyrosis of the extraction residue does not occur during extraction in the extraction apparatus 100.

It is understood from FIG. 4A that the extract by liquefied dimethyl ether in the present embodiment is free from discoloration, hydrolysis, or pyrosis, compared with the components included in the biological material. This is because the extraction using liquefied dimethyl ether is performed at room temperature (for example, 40° C. or lower). Similarly, in FIG. 3 (B), it is understood that the extraction residue by liquid dimethyl ether is free from discoloration, hydrolysis, or pyrosis, compared with the components included in the biological material. This is because the extraction using liquefied dimethyl ether is performed at room temperature (for example, 40° C. or lower).

Based on the above, the extract in the present embodiment contains a water-soluble compound or a lipid-soluble compound of a plant-derived material or an animal-derived material and provides a component included in the material since the compound does not suffer at least one of discoloration, hydrolysis, and pyrosis.

The extraction residue produced by the extraction apparatus 100 contains a water-soluble compound or a lipid-soluble compound of a biologically derived material that is unable to be extracted with the liquefied dimethyl ether 2, and the liquefied dimethyl ether 2 is merely separated from the biologically derived material 7 at room temperature. Based on this, it is clear that the water-soluble compound or the lipid-soluble compound is not denatured. That is, since cell tissue free from heat denaturation can be obtained, the extraction residue can be utilized in the same applications as the applications of the material.

EXAMPLES

The present embodiment will be described more specifically below with reference to examples. However, the present embodiment is not intended to be limited by examples.

Extract and Extraction Residue Produced from Material Having Cell Walls

Example 1

Figure 5:
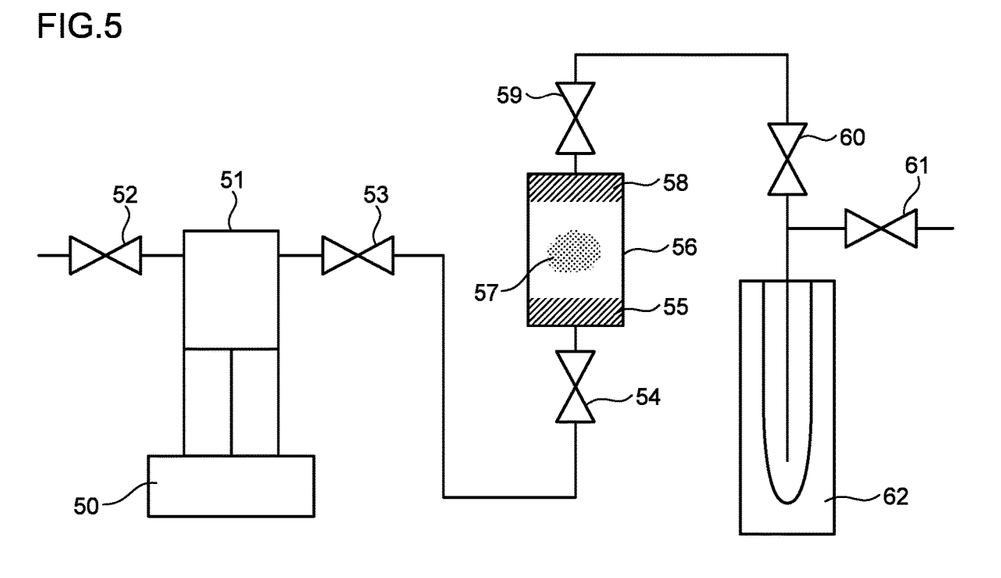
FIG. 5 is a diagram illustrating an extraction apparatus in Examples.

The method of producing an extract and an extraction residue of a plant material was carried out using an extraction apparatus illustrated in FIG. 5 to produce an extract and an extraction residue. Stem lettuce (water content of 10% by mass) was used as a plant material. Stem lettuce is a green vegetable.

Specifically, 3.0 g of stem lettuce 57 was placed in the extraction tank 56 having an internal volume of 10 mL with filters 55 and 58 installed on the upstream side and the downstream side. Subsequently, with the valve 52 opened and the valve 53 closed, dimethyl ether 51 including an auxiliary solvent was charged into the syringe pump 50 and liquefied at 25° C. and 0.7 MPa. The separation tank 62 was purged by dimethyl ether in advance, and the valves 52, 53, 54, 59, 60, and 61 were closed. Water was used as the auxiliary solvent, and the amount of auxiliary solvent added was 5% by mass relative to the liquefied dimethyl ether.

Next, with the valves 53, 54, 59, and 60 opened, liquefied dimethyl ether was supplied using the syringe pump 50. Once the extraction tank 56 was filled with liquefied dimethyl ether, the syringe pump 50 was stopped and with the valves 54 and 59 closed, the stem lettuce 57 was dipped in liquefied dimethyl ether to produce a liquid mixture.

Then, with the valves 54 and 59 opened, liquefied dimethyl ether was supplied again using the syringe pump 50. The flow rate was regulated at 1.0 mL/min (retained for 10 minutes), and 60 mL of the liquid mixture was recovered in the separation tank 62. Subsequently, with the valve 60 closed, the separation tank 62 was removed from the apparatus, and under atmospheric pressure in a predetermined draft, the liquefied dimethyl ether was volatilized to produce an extract.

By repeating the operation above twice, 120 mL of liquefied dimethyl ether including 5% by mass of water in an amount equal to or less than the saturation amount was contacted with the stem lettuce 57 for extraction. Subsequently, with the valve 54 closed and the valves 59, 60, and 61 opened, the pressure in the extraction tank 56 was set to atmospheric pressure, and liquefied dimethyl ether in the extraction tank 56 was exhausted. Thereafter, the stem lettuce 57 after extraction was produced as an extraction residue.

The mass of the extract obtained by completely volatilizing liquefied dimethyl ether was 0.123 g. Using this, the extraction ratio was calculated according to Equation (1) below. The extraction ratio of the extract obtained from the stem lettuce 57 was 4.1% by mass. The color of the extract was green, and it was confirmed by absorptiometry that the extract included chlorophyll which is a green pigment of the material stem lettuce.

Extraction ratio [% by mass]=(the mass of the extract/the mass of the material fed into the extraction tank)×100     Equation (1)

The resultant extraction residue kept the appearance before extraction of stem lettuce which is a plant-derived material, and no damage or discoloration was caused by the extraction operation. The water content of the extraction residue was about 5% by mass.

Example 2

With the same configuration as in Example 1, an extract and an extraction residue were produced from 3.0 g of stem lettuce using liquefied dimethyl ether including no auxiliary solvent, instead of liquefied dimethyl ether including 5% by mass of water in an amount equal to or less than the saturation amount. Then, 0.060 g of an extract was obtained, and the extraction ratio was 2.0% by mass according to Equation (1) above. The color of the extract was green, and it was confirmed by absorptiometry that the extract included chlorophyll which is a green pigment of the material stem lettuce. The resultant extraction residue kept the appearance before extraction of stem lettuce which is a plant-derived material, and no damage or discoloration was caused by the extraction operation. The water content of the extraction residue was about 2% by mass.

Comparative Example 1

Stem lettuce was used as a plant-derived material, and using hexane as an extraction solvent, an extract and an extraction residue were produced at 25° C., 0.1 MPa for 8 hours. It is noted that 25° C. means room temperature and 0.1 MPa means normal atmospheric pressure. Specifically, 3.0 g of stem lettuce and 120 mL of hexane were put into an Erlenmeyer flask and stirred at room temperature under normal atmospheric pressure for 8 hours to produce a liquid mixture of an extract and hexane. Subsequently, the liquid mixture and the stem lettuce were separated by filtration, and the liquid mixture was distilled under a reduced pressure at 30° C. using an evaporator to volatilize hexane to produce an extract. In order to completely volatilize hexane from the stem lettuce after extraction, vacuum drying was performed using a vacuum drier at 30° C. to produce an extraction residue. The weight of the extract obtained from stem lettuce was 0.04 g, and the extraction ratio was 1.3% by mass. The extract was green, same as Example 2, and included chlorophyll. Damage to tissue by stirring was recognized in the resultant extraction residue, compared with the appearance before extraction of stem lettuce which is a plant-derived material, but no discoloration was observed. The water content of the extraction residue was about 1% by mass. This is because water was also volatilized during vacuum drying for volatilizing hexane.

Comparative Example 2

Stem lettuce was used as a plant material, and using hexane heated to 90° C. as an extraction solvent, an extract and an extraction residue were produced at 90° C., 0.1 MPa for 8 hours. It is noted that 0.1 MPa means normal atmospheric pressure. Specifically, 3.0 g of stem lettuce and 120 mL of hexane were put into a round-bottom flask, and hexane was heated to 90° C. in an oil bath. While volatilized hexane was refluxed, extraction was performed under normal atmospheric pressure for 8 hours to obtain a liquid mixture of an extract and hexane. Subsequently, the liquid mixture and the stem lettuce were separated by filtration. The liquid mixture was distilled under a reduced pressure at 30° C. using an evaporator to volatilize hexane to produce an extract. The stem lettuce after extraction was dried under vacuum at 30° C. using a vacuum drier to completely volatilize hexane to produce an extraction residue. The weight of the extract obtained from the stem lettuce was 0.08 g, and the extraction ratio was 2.7% by mass. The color of the extraction liquid was brown, and chlorophyll was reduced compared with Comparative Example 1. This may be because chlorophyll was changed by heat during extraction. The resultant extraction residue discolored from green to brown, compared with the appearance before extraction of stem lettuce which is a plant-derived material. This may be because chlorophyll was changed by pyrolysis. The water content was about 1% by mass. This is because water was also volatilized during vacuum drying for volatilizing hexane.

Figure 6:
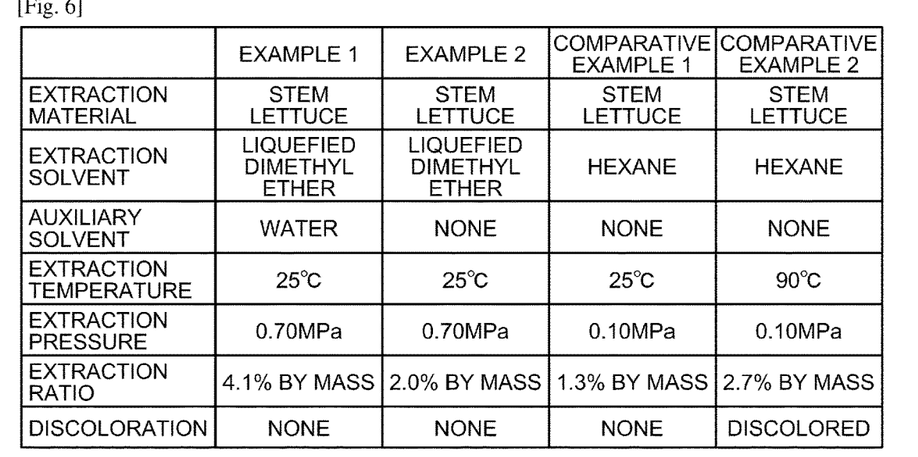
FIG. 6 is a table displaying the extraction ratio and the presence/absence of discoloration of extracts, together with extraction material, extraction solvent, extraction temperature, and extraction pressure.
Figure 7:
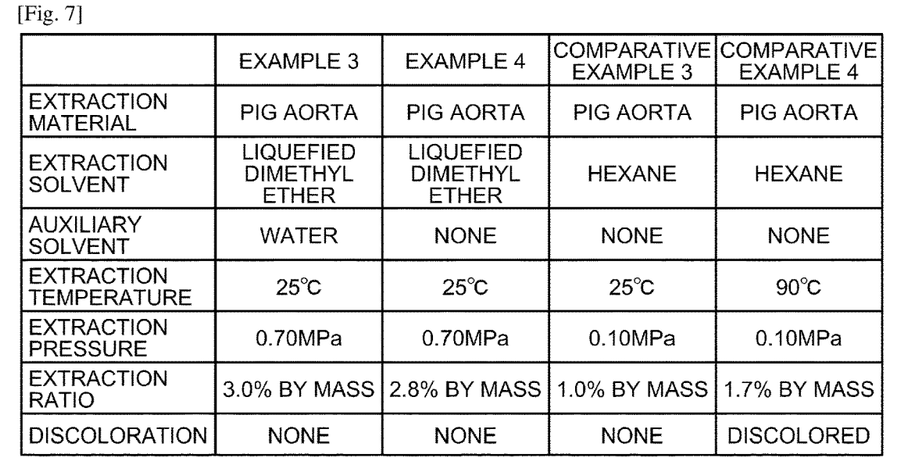
FIG. 7 is a table displaying the extraction ratio and the presence/absence of discoloration of extracts, together with extraction material, extraction solvent, extraction temperature, and extraction pressure.

The extraction ratio and the presence/absence of discoloration of the extracts produced in Example 1, Example 2, Comparative Example 1, and Comparative Example 2 are shown in FIG. 6 together with the extraction material, the extraction solvent, the extraction temperature, and the extraction pressure. It is understood from FIG. 6 that the extracts in Example 1 and Example 2 are not discolored.

In the present embodiment described above, the material having cell walls is a plant-derived material. However, materials derived from fungi such as mushrooms or molds, archaebacteria, eubacteria, having cell walls like plants may be used instead of plants.

Extract and Extraction Residue Produced from Material Having No Cell Walls

Example 3

An extract and an extraction residue were produced under the same conditions as in Example 1 except that pig aorta was used instead of stem lettuce 57. Specifically, first of all, 3.0 g of pig aorta 57 (water content of 70% by weight) was placed as an animal-derived material in the extraction tank 56. Subsequently, with the valve 52 closed and the valve 53 opened, dimethyl ether 51 including an auxiliary solvent was charged into the syringe pump 50 and liquefied at 25° C., 0.7 MPa. The separation tank 62 was purged by dimethyl ether in advance and the valves 52, 53, 54, 59, 60, and 61 were closed. Water was used as the auxiliary solvent, and the amount of auxiliary solvent added was 5% by mass relative to the liquefied dimethyl ether.

Next, with the valves 53, 54, 59, and 60 opened, liquefied dimethyl ether was supplied using the syringe pump 50. Once the extraction tank 56 was filled with liquefied dimethyl ether, the syringe pump 50 was stopped, and with the valves 54 and 59 closed, the pig aorta 57 was dipped in liquefied dimethyl ether to produce a liquid mixture.

With the valves 54 and 59 opened, liquefied dimethyl ether was supplied again using the syringe pump 50. The flow rate was regulated at 1.0 mL/min (retained for 10 minutes), and 60 mL of the liquid mixture was recovered in the separation tank 62. Subsequently, with the valve 60 closed, the separation tank 62 was removed from the apparatus, and under atmospheric pressure in a predetermined draft, the liquefied dimethyl ether was volatilized to produce an extract.

By repeating the operation above 10 times, 600 mL of liquefied dimethyl ether was contacted with pig aorta 57 for extraction. Subsequently, with the valve 54 closed and the valves 59, 60, and 61 opened, the pressure in the extraction tank 56 was set to the atmospheric pressure, whereby liquefied dimethyl ether in the extraction tank 56 was exhausted. Subsequently, the pig aorta 57 after extraction was produced as an extraction residue.

The mass of the resultant extract was measured in a state in which liquefied dimethyl ether was completely volatilized. The weight of the extract obtained from the pig aorta 57 was 0.090 g, and the extraction ratio was 3.0% by mass. The color of the extract was transparent, and the inclusion of phospholipid was confirmed by gas chromatograph. Since phospholipid which is a main component of the cell membrane was detected, it can be assumed that cells are destroyed and nucleic acids are exposed outside the cells.

The resultant extraction residue kept the appearance before extraction of pig aorta which is an animal-derived material and did not exhibit discoloration due to the extraction operation. The water content of the extraction residue was about 5% by mass.

The extraction residue in which cells were destroyed was put into physiological saline including 0.2 mg/mL of DNaseI (manufactured by Roche Diagnostics K.K.) and 0.05 M of $MgCl_2$ (manufactured by Wako Pure Chemical Industries, Ltd.) and shaken in an atmosphere of 4° C. for seven days to decompose nucleic acids.

Next, the extraction residue including decomposed nucleic acids was put into physiological saline including 80% by volume of ethanol and shaken in an atmosphere of 4° C. for three days, and thereafter put into physiological saline and shaken in an atmosphere of 4° C. for one day to obtain decellularized tissue.

Evaluation

As evaluation of the decellularized tissue, the amount of nucleic acids included in the produced decellularized tissue was measured. Using PureLink Genomic DNA Kits (manufactured by Thermo Fisher Scientific Inc.), nucleic acids were extracted from the decellularized tissue and evaluated by a spectrophotometry Nano Drop 2000c (manufactured by Thermo Fisher Scientific Inc.).

The amount of nucleic acids per dry weight included in the decellularized tissue is 2 ng/mg, which is less than the target value 50 ng/mg described in NPL 1, indicating that decellularized tissue serving as a regenerative medical material can be produced from the extraction residue produced in the present embodiment.

Example 4

With the same configuration as in Example 3, an extract and an extraction residue were produced from 3.0 g of pig aorta using liquefied dimethyl ether including no auxiliary solvent, instead of liquefied dimethyl ether including 5% by mass of water in an amount equal to or less than the saturation amount. Then, 0.084 g of an extract was obtained, and the extraction ratio was 2.8% by mass. The color of the extract was transparent. The resultant extraction residue kept the appearance before extraction of pig aorta which is an animal-derived material and exhibited no discoloration in the extraction operation. The water content of the extraction residue was about 2% by mass.

Comparative Example 3

Pig aorta was used as an animal-derived material, and using hexane as an extraction solvent, an extract and an extraction residue were produced at 25° C., 0.1 MPa for 8 hours. It is noted that 25° C. represents room temperature, and 0.1 MPa means normal atmospheric pressure. Specifically, 3.0 g of pig aorta and 120 mL of hexane were put into an Erlenmeyer flask and stirred at room temperature under normal atmospheric pressure for 8 hours to obtain a liquid mixture of an extract and hexane. Subsequently, the pig aorta was removed from the liquid mixture, and the liquid mixture was distilled under a reduced pressure at 30° C. using an evaporator to volatilize hexane to produce an extract. In order to completely volatilize hexane from the pig aorta after extraction, vacuum drying was performed using a vacuum drier at 30° C. to produce an extraction residue. The weight of the extract obtained from pig aorta was 0.03 g, and the extraction ratio was 1.0% by mass. The color of the extract was transparent, same as Example 3. The resultant extraction residue exhibited no discoloration, compared with the appearance before extraction of pig aorta which is an animal-derived material. The water content of the extraction residue was about 1% by mass. This is because water was also volatilized during vacuum drying for volatilizing hexane.

Comparative Example 4

Pig aorta was used as an animal-derived material, and using hexane heated to 90° C. as an extraction solvent, an extract and an extraction residue were produced at 90° C., 0.1 MPa for 8 hours. It is noted that 0.1 MPa means normal atmospheric pressure. Specifically, 3.0 g of pig aorta and 120 mL of hexane were put into a round-bottom flask, and hexane was heated to 90° C. in an oil bath. While volatilized hexane was refluxed, extraction was performed under normal atmospheric pressure for 8 hours to obtain a liquid mixture of an extract and hexane. Subsequently, the pig aorta was removed from the liquid mixture, and the liquid mixture was distilled under a reduced pressure at 30° C. using an evaporator to volatilize hexane to produce an extract. The pig aorta after extraction was dried under vacuum at 30° C. using a vacuum drier to completely volatilize hexane to produce an extraction residue. The weight of the extract obtained from pig aorta was 0.05 g, and the extraction ratio was 1.7% by mass. The color of the extraction liquid was white, and the resultant extraction residue discolored from white to brown, compared with the appearance before extraction of pig aorta which is an animal-derived material. This is because protein was heat-denatured by heat during extraction. The water content was about 1% by mass. This is because water was also volatilized during vacuum drying for volatilizing hexane.

The extraction ratio and the presence/absence of discoloration of the extracts produced in Example 3, Example 4, Comparative Example 3, and Comparative Example 4 are shown in FIG. 5 together with the extraction material, the extraction solvent, the extraction temperature, and the extraction pressure. It is understood from FIG. 5 that the extract in Example 3 is not discolored. Since hexane is a solvent hazardous to human bodies, it is impossible to use the extraction residue produced by hexane extraction as a regenerative medical material.

Extract and Extraction Residue Produced from Material Having Cell Walls

Example 5

An extract and an extraction residue were produced from a plant-derived material using the extraction apparatus illustrated in FIG. 5. Specifically, 5.0 g of grape seed 57, as a plant-derived material, ground to a length equal to or smaller than about 1 mm was placed in the extraction tank 56 having an internal volume of 10 mL with filters 55 and 58 installed on the upstream side and the downstream side. Subsequently, with the valve 52 closed and the valve 53 opened, dimethyl ether 51 was charged into the syringe pump 50 and liquefied at 25° C., 0.7 MPa. The separation tank 62 was purged by dimethyl ether in advance and the valves 52, 53, 54, 59, 60, and 61 were closed. The extraction apparatus illustrated in FIG. 5 is configured such that dimethyl ether is not circulated in the extraction apparatus 100 illustrated in FIG. 1.

Next, with the valves 53, 54, 59, and 60 opened, liquefied dimethyl ether was supplied using the syringe pump 50. Once the extraction tank 56 was filled with liquefied dimethyl ether, the syringe pump 50 was stopped, and with the valves 54 and 59 closed, the grape seed 57 was dipped in liquefied dimethyl ether to produce a liquid mixture.

With the valves 54 and 59 opened, liquefied dimethyl ether was supplied again using the syringe pump 50. The flow rate was regulated at 1.0 mL/min (retained for 10 minutes), and 60 mL of the liquid mixture was recovered in the separation tank 62. Subsequently, with the valve 60 closed, the separation tank 62 was removed from the apparatus, and under atmospheric pressure in a predetermined draft, liquefied dimethyl ether was volatilized to produce an extract.

By repeating the operation above twice, 120 mL of liquefied dimethyl ether was contacted with the grape seed 57 for extraction. Subsequently, with the valve 54 closed and the valves 59, 60, and 61 opened, the pressure in the extraction tank 56 was set to atmospheric pressure, and the liquefied dimethyl ether in the extraction tank 56 was exhausted. Subsequently, the grape seed 57 after extraction was produced as an extraction residue.

The mass of the resultant extract was measured in a state in which liquefied dimethyl ether was completely volatilized, and the extraction ratio was calculated according to Equation (2) below. The weight of the extract obtained from the grape seed 57 was 0.88 g, and the extraction ratio was 17.6% by mass. The appearance of the extract was a mixture of red solid and yellow oil. A red natural pigment compound anthocyanin and an antioxidant compound proanthocyanidin were detected as polyphenols by liquid chromatography. Fatty acids, such as linoleic acid, palmitic acid, oleic acid, and stearic acid were detected by gas chromatograph. The flavor of the extract was the same as the flavor of the grape seed 57 before extraction.

$$\text{Extraction ratio [\% by mass]} = (\text{the mass of the extract/the mass of the plant-derived material fed into the extraction tank}) \times 100 \quad \text{Equation (2)}$$

The resultant extraction residue kept the shape before extraction, and no damage or change of tissue due to the extraction operation was observed. That is, it is understood that cellulose, hemicellulose, and lignin, which are main components of the cell wall components of the grape seed 57, were not affected by liquefied dimethyl ether. The water content of the extraction residue was about 5% by mass.

In this way, the extraction residue can provide cell tissue free from denaturation by heat and therefore can be utilized while keeping the original property of cell tissue. For example, the extraction residue obtained by extracting cell components from pig skin contains collagen as a main component and is not denatured by heat, and thus can be utilized as a material of collagen powder.

The extraction residue contains cell wall components such as cellulose, hemi-cellulose, and lignin and thus can be utilized as a material of paper and dietary fibers.

The extraction residue has a water content as low as about 5% by mass and thus can be utilized as a flammable, high-quality fuel. When grape seed before extraction and the extraction residue were kept at room temperature for 60 days, the grape seed before extraction molded, whereas the extraction residue did not mold and was more preservative. This may be because bacteria and germs were removed because of the contact with liquefied dimethyl ether.

Example 6

An extract and an extraction residue were produced using stem lettuce instead of grape seed 57, in the same manner as in Example 5. Specifically, first of all, 3.0 g of stem lettuce 57 as a plant-derived material was placed in the extraction tank 56. Subsequently, with the valve 52 closed and the valve 53 opened, dimethyl ether 51 was charged into the syringe pump 50 and liquefied at 25° C., 0.7 MPa. The separation tank 62 was purged by dimethyl ether in advance and the valves 52, 53, 54, 59, 60, and 61 were closed. Water was used as the auxiliary solvent, and the amount of auxiliary solvent added was 5% by mass relative to the liquefied dimethyl ether.

Next, with the valves 53, 54, 59, and 60 opened, liquefied dimethyl ether was supplied using the syringe pump 50. Once the extraction tank 56 was filled with liquefied dimethyl ether, the syringe pump 50 was stopped, and with the valves 54 and 59 closed, the stem lettuce 57 was dipped in liquefied dimethyl ether to produce a liquid mixture.

With the valves 54 and 59 opened, liquefied dimethyl ether was supplied again using the syringe pump 50. The flow rate was regulated at 1.0 mL/min (retained for 10 minutes), and 60 mL of a liquid mixture was recovered in the separation tank 62. Subsequently, with the valve 60 closed, the separation tank 62 was removed from the apparatus, and under atmospheric pressure in a predetermined draft, liquefied dimethyl ether was volatilized to produce an extract.

By repeating the operation above twice, 120 mL of liquefied dimethyl ether including 5% by mass of water in an amount equal to or less than the saturation amount was contacted with the stem lettuce 57 for extraction. Subsequently, with the valve 54 closed and the valves 59, 60, and 61 opened, the pressure in the extraction tank 56 was set to atmospheric pressure, whereby liquefied dimethyl ether in the extraction tank 56 was exhausted. Subsequently, the stem lettuce 57 after extraction was produced as an extraction residue.

The mass of the resultant extract was measured in a state in which liquefied dimethyl ether was completely volatilized. The weight of the extract obtained from the stem lettuce 57 was 0.12 g, and the extraction ratio was 4.1% by mass. The color of the extract was green, and it was confirmed by absorptiometry that the extract included chlorophyll which is a green pigment of the material stem lettuce.

The resultant extraction residue kept the appearance before extraction of stem lettuce which is a plant-derived material, and no damage or discoloration of tissue occurred in the extraction operation. The water content of the extraction residue was about 5% by mass.

Example 7

With the same configuration as in Example 6, an extract and an extraction residue were produced from 3.0 g of stem lettuce using liquefied dimethyl ether including no auxiliary solvent, instead of liquefied dimethyl ether including 5% by mass of water in an amount equal to or less than the saturation amount. Then, 0.060 g of an extract was obtained, and the extraction ratio was 2.0% by mass according to Equation (2) above. The color of the extract was green, and it was confirmed by absorptiometry that the extract included chlorophyll which is a green pigment of the material stem lettuce. The resultant extraction residue kept the appearance before extraction of stem lettuce which is a plant-derived material, and no damage or discoloration occurred in the extraction operation. The water content of the extraction residue was about 2% by mass.

The total polyphenols of the extracts produced in Example 6 and Example 7 were determined by the Folin-Ciocalteu method. The compositions of total polyphenols in the extracts in Example 6 and Example 7 were about 15% by mass and about 5% by mass, respectively. The extract produced in Example 6 had a higher ratio of polyphenol than the extract produced in Example 7. This may be because the liquefied dimethyl ether can dissolve more water-soluble compound because of water added as an auxiliary solvent. In this way, the extract produced by liquefied dimethyl ether including an auxiliary solvent has a high component ratio of water-soluble compound, and the extract produced by liquefied dimethyl ether including no auxiliary solvent has a high component ratio of lipid-soluble compound.

Comparative Example 5

Stem lettuce was used as a plant-derived material, and using hexane as an extraction solvent, an extract and an extraction residue were produced at 25° C., 0.1 MPa for 8 hours. It is noted that 25° C. represents room temperature, and 0.1 MPa means normal atmospheric pressure. Specifically, 3.0 g of stem lettuce and 120 mL of hexane were put into an Erlenmeyer flask and stirred at room temperature under normal atmospheric pressure for 8 hours to produce a liquid mixture of an extract and hexane. Subsequently, the liquid mixture and the stem lettuce were separated by filtration, and the liquid mixture was distilled under a reduced pressure at 30° C. using an evaporator to volatilize hexane to produce an extract. In order to completely volatilize hexane from the stem lettuce after extraction, vacuum drying was performed at 30° C. using a vacuum drier to produce an extraction residue. The weight of the extract obtained from the stem lettuce was 0.04 g, and the extraction ratio was 1.3% by mass. The extract was green, same as Example 6, and included chlorophyll. For the resultant extraction residue, damage of tissue due to stirring was observed, compared with the appearance before extraction of stem lettuce which is a plant-derived material, but no discoloration was observed. The water content of the extraction residue was about 1% by mass. This is because water was also volatilized during vacuum drying for volatilizing hexane.

Comparative Example 6

Stem lettuce was used as a plant material, and using hexane heated to 90° C. as an extraction solvent, an extract and an extraction residue were produced at 90° C., 0.1 MPa for 8 hours. It is noted that 0.1 MPa means normal atmospheric pressure. Specifically, 3.0 g of stem lettuce and 120 mL of hexane were put into a round-bottom flask, and hexane was heated to 90° C. in an oil bath. While volatilized hexane was refluxed, extraction was performed under normal atmospheric pressure for 8 hours to obtain a liquid mixture of an extract and hexane. Subsequently, the liquid mixture and the stem lettuce were separated by filtration. The liquid mixture was distilled under a reduced pressure at 30° C. using an evaporator to volatilize hexane to produce an extract. The stem lettuce after extraction was dried under vacuum at 30° C. using a vacuum drier to completely volatilize hexane to produce an extraction residue. The weight of the extract obtained from the stem lettuce was 0.08 g, and the extraction ratio was 2.7% by mass. The color of the extraction liquid was brown, and chlorophyll was reduced compared with Comparative Example 5. This may be because chlorophyll was changed by heat during extraction. The resultant extraction residue discolored from green to brown, compared with the appearance before extraction of stem lettuce which is a plant-derived material. This may be because chlorophyll was changed by pyrolysis. The water content was about 1% by mass. This is because water was also volatilized during vacuum drying for volatilizing hexane.

Figure 8:
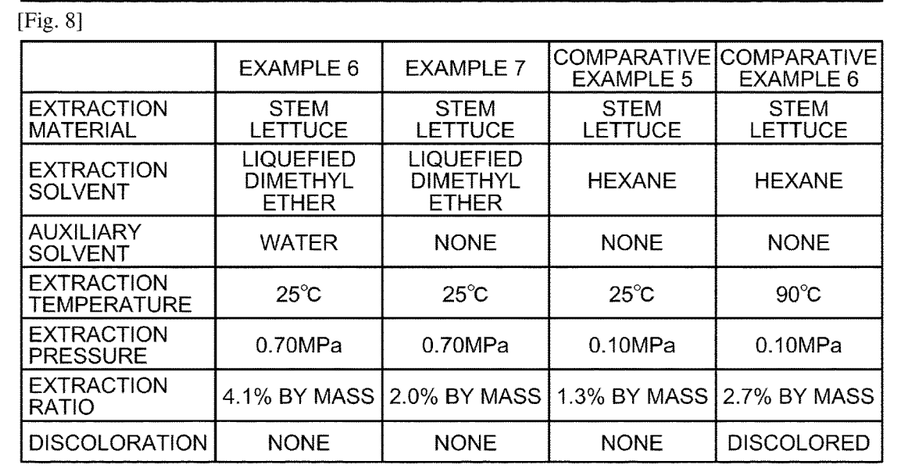
FIG. 8 is a table displaying the presence/absence of denaturation and discoloration of extracts produced in Example 6, Example 7, Comparative Example 5, and Comparative Example 6, together with extraction material, extraction solvent, extraction temperature, and extraction pressure.

The extraction ratio and the presence/absence of discoloration of the extracts produced in Example 6, Example 7, Comparative Example 5, and Comparative Example 6 are shown in FIG. 8 together with the extraction material, the extraction solvent, the extraction temperature, and the extraction pressure. It is understood from FIG. 8 that the extracts and the extraction residues in Example 6 and Example 7 are not discolored.

Example 8

An extract and an extraction residue were produced under the same conditions as in Example 1 except that pig aorta was used instead of stem lettuce 57. Specifically, first of all, 3.0 g of pig aorta 57 (water content of 70% by weight) was placed as an animal-derived material in the extraction tank 56. Subsequently, with the valve 52 closed and the valve 53 opened, dimethyl ether 51 including an auxiliary solvent was charged into the syringe pump 50 and liquefied at 25° C., 0.7 MPa. The separation tank 62 was purged by dimethyl ether in advance, and the valves 52, 53, 54, 59, 60, and 61 were closed. Water was used as an auxiliary solvent, and the amount of auxiliary solvent added was 5% by mass relative to the liquefied dimethyl ether.

Next, with the valves 53, 54, 59, and 60 opened, liquefied dimethyl ether was supplied using the syringe pump 50. Once the extraction tank 56 was filled with liquefied dimethyl ether, the syringe pump 50 was stopped, and with the valves 54 and 59 closed, the pig aorta 57 was dipped in liquefied dimethyl ether to produce a liquid mixture.

With the valves 54 and 59 opened, liquefied dimethyl ether was supplied again using the syringe pump 50. The flow rate was regulated at 1.0 mL/min (retained for 10 minutes), and 60 mL of the liquid mixture was recovered in the separation tank 62. Subsequently, with the valve 60 closed, the separation tank 62 was removed from the apparatus, and under atmospheric pressure in a predetermined draft, liquefied dimethyl ether was volatilized to produce an extract.

By repeating the operation above 10 times, 600 mL of liquefied dimethyl ether was contacted with the pig aorta 57 for extraction. Subsequently, with the valve 54 closed and the valves 59, 60, and 61 opened, the pressure in the extraction tank 56 was set to the atmospheric pressure, whereby liquefied dimethyl ether in the extraction tank 56 was exhausted. Subsequently, the pig aorta 57 after extraction was produced as an extraction residue.

The mass of the resultant extract was measured in a state in which liquefied dimethyl ether was completely volatilized. The weight of the extract obtained from the pig aorta 57 was 0.090 g, and the extraction ratio was 3.0% by mass. The color of the extract was transparent, and the inclusion of phospholipid was confirmed by gas chromatograph.

The resultant extraction residue kept the appearance before extraction of pig aorta which is an animal-derived material, and no discoloration occurred in the extraction operation. The water content of the extraction residue was about 5% by mass.

Example 9

With the same configuration as in Example 8, an extract and an extraction residue were produced from 3.0 g of pig aorta using liquefied dimethyl ether including no auxiliary solvent, instead of liquefied dimethyl ether including 5% by mass of water in an amount equal to or less than the saturation amount. Then, 0.084 g of an extract was obtained, and the extraction ratio was 2.8% by mass. The color of the extract was transparent. The resultant extraction residue kept the appearance before extraction of pig aorta which is an animal-derived material, and no discoloration occurred in the extraction operation. The water content of the extraction residue was about 2% by mass.

Comparative Example 7

Pig aorta was used as an animal-derived material, and using hexane as an extraction solvent, an extract and an extraction residue were produced at 25° C., 0.1 MPa for 8 hours. It is noted that 25° C. represents room temperature and 0.1 MPa means normal atmospheric pressure. Specifically, 3.0 g of pig aorta and 120 mL of hexane were put into an Erlenmeyer flask and stirred at room temperature under normal atmospheric pressure for 8 hours to obtain a liquid mixture of an extract and hexane. Subsequently, the pig aorta was removed from the liquid mixture, and the liquid mixture was distilled under a reduced pressure at 30° C. using an evaporator to volatilize hexane to produce an extract. In order to completely volatilize hexane from the pig aorta after extraction, vacuum drying was performed at 30° C. using a vacuum drier to produce an extraction residue. The weight of the extract obtained from the pig aorta was 0.03 g, and the extraction ratio was 1.0% by mass. The color of the extract was transparent, same as Example 3. The resultant extraction residue did not exhibit discoloration, compared with the appearance before extraction of pig aorta which is an animal-derived material. The water content of the extraction residue was about 1% by mass. This is because water was also volatilized during vacuum drying for volatilizing hexane.

Comparative Example 8

Pig aorta was used as an animal-derived material, and using hexane heated to 90° C. as an extraction solvent, an extract and an extraction residue were produced at 90° C., 0.1 MPa for 8 hours. It is noted that 0.1 MPa means normal atmospheric pressure. Specifically, 3.0 g of pig aorta and 120 mL of hexane were put into a round-bottom flask, and hexane was heated to 90° C. in an oil bath. While volatilized hexane was refluxed, extraction was performed under normal atmospheric pressure for 8 hours to obtain a liquid mixture of an extract and hexane. Subsequently, the pig aorta was removed from the liquid mixture, and the liquid mixture was distilled under a reduced pressure at 30° C. using an evaporator to volatilize hexane to produce an extract. The pig aorta after extraction was dried under vacuum at 30° C. using a vacuum drier to completely volatilize hexane to produce an extraction residue. The weight of the extract obtained from the pig aorta was 0.05 g, and the extraction ratio was 1.7% by mass. The color of the extraction liquid was white, and the resultant extraction residue discolored from white to brown, compared with the appearance before extraction of pig aorta which is an animal-derived material. This may be because protein was heat-denatured by heat during extraction. The water content was about 1% by mass. This is because water was also volatilized during vacuum drying for volatilizing hexane.

Figure 9:
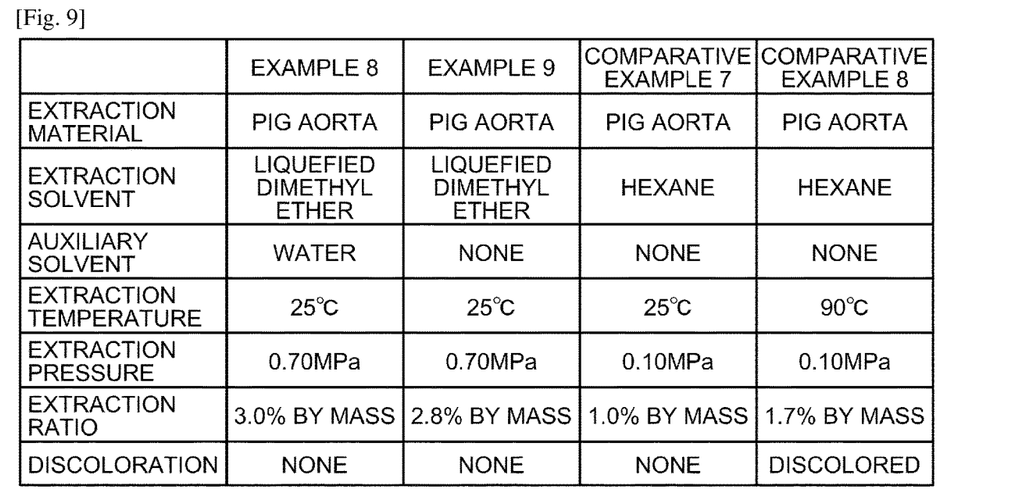
FIG. 9 is a table displaying the presence/absence of denaturation and discoloration of extracts produced in Example 8, Example 9, Comparative Example 7, and Comparative Example 8, together with extraction material, extraction solvent, extraction temperature, and extraction pressure. The accompanying drawings are intended to depict exemplary embodiments of the present invention and should not be interpreted to limit the scope thereof. Identical or similar reference numerals designate identical or similar components throughout the various drawings.

The extraction ratio and the presence/absence of discoloration of the extracts produced in Example 8, Example 9, Comparative Example 7, and Comparative Example 8 are shown in FIG. 9 together with the extraction material, the extraction solvent, the extraction temperature, and the extraction pressure. It is understood from FIG. 9 that the extracts and the extraction residues in Example 8 and Example 9 are not discolored.

As described above, in the method of producing an extract and an extraction residue of a biological material above, in the extraction process, a component in the biological material is extracted using liquefied dimethyl ether for the biological material to obtain a liquefied dimethyl ether solution including the component. Biologically derived moisture and water-soluble compound thus can be extracted well. In addition, an extraction residue from which moisture and the extract are well removed can be obtained. A water-soluble natural component can be provided since the extract contains water-soluble and lipid-soluble natural components and is not denatured by pyrosis.

The above-described embodiment is illustrative and does not limit the present invention. Thus, numerous additional modifications and variations are possible in light of the above teachings. For example, at least one element of different illustrative and exemplary embodiment herein may be combined with each other or substituted for each other within the scope of this disclosure and appended claims. Further, features of components of the embodiment, such as the number, the position, and the shape are not limited the embodiment and thus may be preferably set. It is therefore to be understood that within the scope of the appended claims, the disclosure of the present invention may be practiced otherwise than as specifically described herein.

REFERENCE SIGNS LIST

1 Storage tank
2 Liquefied dimethyl ether
6 Extraction tank
11 Separation tank
100 Extraction apparatus

CITATION LIST

Patent Literature

PTL 1: Japanese Laid-open Patent Publication No. 2010-240609
PTL 2: Japanese Laid-open Patent Publication No. 2001-106636

Non Patent Literature

NPL 1: Biomaterials 32 (2011) 3233-3243

The invention claimed is:

1. A method of producing an extraction residue of a biological material, the method comprising:
feeding the biological material into an extraction tank having a filter disposed on an upstream side and a filter disposed on a downstream side, wherein the upstream side is connected to a storage tank containing liquefied dimethyl ether by a first conduit having a first valve and the downstream side is connected directly to a separation tank by a second conduit having a second valve, wherein the first valve and the second valve are closed during the feeding of the biological material into the extraction tank, wherein the biological material is an animal-derived material;
opening the first valve to allow the liquefied dimethyl ether in the storage tank to be fed into the extraction tank through the first conduit and subsequently closing the first valve;
extracting a component in the biological material using liquefied dimethyl ether for dissolving the biological material to obtain a liquefied dimethyl ether solution including the component;
opening the first valve and the second valve, thereby providing fresh liquefied dimethyl ether from the storage tank by the first conduit and feeding the liquefied dimethyl ether solution including the component only to the separation tank by the second conduit;
volatilizing or otherwise separating dimethyl ether from the liquefied dimethyl ether solution in the separation tank to obtain an extraction residue;
decomposing a nucleic acid component included in the extraction residue using a nuclease; and
removing the nucleic acid component from the extraction residue.

2. The method of producing an extraction residue of a biological material according to claim 1, wherein
the liquefied dimethyl ether is admixed with an auxiliary solvent in an amount equal to or less than a saturation amount of the liquefied dimethyl ether, wherein the amount of the auxiliary solvent is equal to or less than 7% by mass relative to the liquefied dimethyl ether.

3. The method of producing an extraction residue of a biological material according to claim 2, wherein
the auxiliary solvent is water or alcohol.

* * * * *